United States Patent [19]
Evans et al.

[11] Patent Number: 6,022,897
[45] Date of Patent: Feb. 8, 2000

[54] SELECTIVE MODULATORS OF PEROXISOME PROLIFERATOR ACTIVATED RECEPTOR-GAMMA, AND METHODS FOR THE USE THEREOF

[75] Inventors: Ronald M. Evans; Barry M. Forman, both of La Jolla, Calif.

[73] Assignee: The Salk Institute for Biological Studies, La Jolla, Calif.

[21] Appl. No.: 08/465,375

[22] Filed: Jun. 5, 1995

Related U.S. Application Data

[63] Continuation-in-part of application No. 08/428,559, Apr. 25, 1995, abandoned.

[51] Int. Cl.[7] ........................ A61K 31/19; A61K 31/015; A61K 31/01
[52] U.S. Cl. .......................... 514/573; 514/763; 514/768
[58] Field of Search .................................... 514/573, 763, 514/768

[56] References Cited

U.S. PATENT DOCUMENTS

| | | | |
|---|---|---|---|
| 4,016,184 | 4/1977 | Morton, Jr. ............................. | 260/408 |
| 4,049,678 | 9/1977 | Peterson ............................ | 260/343.41 |

OTHER PUBLICATIONS

Bardot et al., "PPAR–RXR Heterodimer Activates a Peroxisome Proliferator Response Element Upstream of the Bifunctional Enzyme Gene" *Biochem. Biophys. Res. Comm.* 192(1):37–45 (1993).

Berger et al., "Interaction of Glucocorticoid Analogues with the Human Glucocorticoid receptor" *J. Steroid Biochem. Molec. Biol.* 41(3–8):733–738 (1992).

Gearing et al., "Interaction of the Peroxisome–Proliferator–Activated Receptor and Retinoid X Receptor" *Proc. Natl. Acad. Sci. USA* 90:1440–1444 (1993).

Giguere et al., "Identification of a Receptor for the Morphogen Retinoic Acid" *Nature* 330:624–629 (1987).

Gottlicher et al., "Fatty Acids Activate a Chimera of the Clofibric Acid–Activated Receptor and the Glucocorticoid Receptor" *Proc. Natl. Acad. Sci. USA* 89:4653–4657 (1992).

Hall et al., "Expression and Regulation of *Escherichia coli* lacZ Gene Fusions in Mammalian Cells" *J. Mol. Appl. Genet* 2(1):101–109 (1983).

Heyman et al., "9–Cis Retinoic Acid is a High Affinity Ligand for the Retinoid X Receptor" *Cell* 68:397–406 (1992).

Hollenberg and Evans, "Multiple and Cooperative Trans–Activation Domains of the Human Glucocorticoid Receptor" *Cell* 55:899–906 (1988).

Issemann and Green, "Activation of a Member of the Steroid Hormone Receptor Superfamily by Peroxisome Proliferators" *Nature* 347:645–650 (1990).

Keegan et al., "Separation of DNA Binding from the Transcription–Activating Function of a Eukaryotic Regulatory Protein" *Science* 231:699–704 (1986).

Keller et al., "Fatty Acids and Retinoids Control Lipid Metabolism Through Activation of Peroxisome Proliferator–Activated Receptor–Retinoid X Receptor Heterodimers" *Proc. Natl. Acad. Sci. USA* 90:2160–2164 (1993).

Kliewer et al., "Convergence of 9–cis Retinoic Acid and Peroxisosme Proliferator Signalling Pathways Through Heterodimer Formation of Their Receptors" *Nature* 358:771–774 (1992).

Lazarow and Fujiki, "Biogenesis of Peroxisomes" *Ann. Rev. Cell Biol.* 1:489–530 (1985).

Levin et al., "9–Cis Retinoic Acid Stereoisomer Binds and Activates the Nuclear Receptor RXRα" *Nature* 355:359–361 (1992).

Luckow and Schütz, "CAT constructions with multiple unique restriction sites for the functional analysis of eukaryotic promoters and regulatory elements" *Nucleic Acid Research* 15(13):5490 (1987).

Mangelsdorf et al., "Nuclear receptor that identifies a novel retinoic acid response pathway" *Nature* 345:224–229 (1990).

Marcus et al., "Diverse Peroxisome Proliferator–Activated Receptors Bind to the Peroxisome Proliferator–Response Elements of the Rat Hydratase/Dehydrogenase and Fatty Acyl–CoA Oxidase Genes but Differentially Induce Expression" *Proc. Natl. Acad. Sci. USA* 90:5723–5727 (1993).

Muerhoff et al., "The Peroxisome Proliferator–Activated Receptor mediates the Induction of CYP4A6, a Cytochrome P450 Fatty Acid ω–Hydroxylase, by Clofibric Acid" *J. Biol. Chem.* 267(27):19051–19053 (1992).

Nemali et al., "Comparison of Constitutive and Inducible Levels of Expression of Peroxisomal β–Oxidation and Catalase Genes in Liver and Extrahepatic Tissues of Rat" *Cancer Res.* 48:5316–5324 (1988).

Reddy and Lalwani, "Carcinogenesis by Hepatic Peroxisome Proliferators: Evaluation of the Risk of Hypolipidemic Drugs and Industrial Plasticizers to Humans" *Crit. Rev. Toxicol.* 12(1):1–58 (1983).

Sadowski and Ptashne, "A vector for expressing GAL4 (1–147) fusions in mammalian cells" *Nucleic Acids Research* 17(18):7539 (1989).

Tugwood et al., "The Mouse Peroxisome Proliferator Activated Receptor Recognizes a Response Element in the 5' Flanking Sequence of the Rat Acyl CoA Oxidase Gene" *EMBO J.* 11(2):433–439 (1992).

(List continued on next page.)

*Primary Examiner*—Theodore J. Criares
*Attorney, Agent, or Firm*—Gray, Cary, Ware & Freidenrich; Stephen E. Reiter; David F. Kleinsmith

[57] ABSTRACT

In accordance with the present invention, there are provided a class of compounds which are capable of selectively modulating processes mediated by peroxisome proliferator activated receptor-gamma (PPAR-γ). The identification of such compounds makes possible the selective intervention in PPAR-γ mediated pathways, without exerting inadvertent effects on pathways mediated by other PPAR isoforms.

15 Claims, 2 Drawing Sheets

OTHER PUBLICATIONS

Umesono et al., "Direct Repeats as Selective Response Elements for the Thyroid Hormone, Retinoic Acid, and Vitamin $D_3$ Receptors" *Cell* 65:1255–1266 (1991).

Vamecq and Draye, "Pathophysiology of Peroxisomal β–Oxidation" *Essays Biochem.* 24:115–225 (1989).

Webster et al., "The Hormone–Binding Domains of the Estrogen and Glucocorticoid Receptors Contain an Inducible Transcription Activation Function" *Cell* 54:199–207 (1988).

Forman et al., "15–Deoxy–Delta$^{12, 14}$–Prostaglandin $J_2$ Is a Ligand for the Adipocyte Determination Factor PPAR Gamma" *Cell* 83:803–812 (1995).

Greene et al., "Isolation of the Human Peroxisome Proliferator Activated Receptor Gamma cDNA: Expression in Hematopoietic Cells and chromosomal Mapping" *Gene Expression* 4:281–299 (1995).

Kliewer et al., "Differential expression and activation of a family of murine peroxisome proliferator–activated receptors" *Proc. Natl. Acad. Sci. USA* 91:7355–7359 (1994).

Kliewer et al., "A Prostaglandin $J_2$ Metabolite Binds Peroxisome Proliferator–Activated Receptor Gamma and Promotes Adipocyte Differentiation" *Cell* 83:813–819 (1995).

Lehmann et al., An antidiabetic Thiazolidinedione Is a High Affinity Ligand for Peroxisome Proliferator–activated Receptor Gamma(PPAR–Gamma) 270(22):12953–12956 (1995).

Yu et al., "Differential Activation of Peroxisome Proliferator–activated Receptors by Eicosanoids" *J. Biol. Chem.* 270(41):23975–23983 (1995).

Activation of PPARγ by Prostaglandins

SEQUENCE LISTING

<160> NUMBER OF SEQ ID NOS: 7

<210> SEQ ID NO 1
<211> LENGTH: 2005
<212> TYPE: DNA
<213> ORGANISM: Mus musculus
<220> FEATURE:
<221> NAME/KEY: CDS
<222> LOCATION: (352)...(1776)

<400> SEQUENCE: 1

```
atcgaatccc gcgccccagg cgctgccgct ctgagtgcga cgggccccgc ctggccggcc      60
ggaggacgcg gaagaagaga cctggggcgc tgcctggggt attgggtcgc gcgcagtgag     120
gggaccgagt gtgacgacaa ggtgaccggg ctgaggggac gggctgagga gaagtcacac     180
```

```
tctgacagga gcctgtgaga ccaacagcct gacggggtct cggttgaggg gacgcgggct      240
gagaagtcac gttctgacag gactgtgtga cagacaagat ttgaaagaag cggtgaacca      300
ctgatattca ggacattttt aaaaacaaga ctacccttta ctgaaattac c atg gtt      357
                                                        Met Val
                                                         1 gac aca gag atg cca ttc tgg ccc acc aac ttc gga atc agc tct gtg        405
Asp Thr Glu Met Pro Phe Trp Pro Thr Asn Phe Gly Ile Ser Ser Val
         5                  10                  15 gac ctc tcc gtg atg gaa gac cac tcg cat tcc ttt gac atc aag ccc        453
Asp Leu Ser Val Met Glu Asp His Ser His Ser Phe Asp Ile Lys Pro
     20                  25                  30 ttt acc aca gtt gat ttc tcc agc att tct gct cca cac tat gaa gac        501
Phe Thr Thr Val Asp Phe Ser Ser Ile Ser Ala Pro His Tyr Glu Asp
 35                  40                  45                  50 att cca ttc aca aga gct gac cca atg gtt gct gat tac aaa tat gac        549
Ile Pro Phe Thr Arg Ala Asp Pro Met Val Ala Asp Tyr Lys Tyr Asp
                 55                  60                  65 ctg aag ctc caa gaa tac caa agt gcg atc aaa gta gaa cct gca tct        597
Leu Lys Leu Gln Glu Tyr Gln Ser Ala Ile Lys Val Glu Pro Ala Ser
             70                  75                  80 cca cct tat tat tct gaa aag acc cag ctc tac aac agg cct cat gaa        645
Pro Pro Tyr Tyr Ser Glu Lys Thr Gln Leu Tyr Asn Arg Pro His Glu
         85                  90                  95 gaa cct tct aac tcc ctc atg gcc att gag tgc cga gtc tgt ggg gat        693
Glu Pro Ser Asn Ser Leu Met Ala Ile Glu Cys Arg Val Cys Gly Asp
    100                 105                 110 aaa gca tca ggc ttc cac tat gga gtt cat gct tgt gaa gga tgc aag        741
Lys Ala Ser Gly Phe His Tyr Gly Val His Ala Cys Glu Gly Cys Lys
115                 120                 125                 130 ggt ttt ttc cga aga acc atc cga ttg aag ctt att tat gat agg tgt        789
Gly Phe Phe Arg Arg Thr Ile Arg Leu Lys Leu Ile Tyr Asp Arg Cys
                135                 140                 145 gat ctt aac tgc cgg atc cac aaa aaa agt aga aat aaa tgt cag tac        837
Asp Leu Asn Cys Arg Ile His Lys Lys Ser Arg Asn Lys Cys Gln Tyr
            150                 155                 160 tgt cgg ttt cag aag tgc ctt gct gtg ggg atg tct cac aat gcc atc        885
Cys Arg Phe Gln Lys Cys Leu Ala Val Gly Met Ser His Asn Ala Ile
        165                 170                 175 agg ttt ggg cgg atg cca cag gcc gag aag gag aag ctg ttg gcg gag        933
Arg Phe Gly Arg Met Pro Gln Ala Glu Lys Glu Lys Leu Leu Ala Glu
    180                 185                 190 atc tcc agt gat atc gac cag ctg aac cca gag tct gct gat ctg cga        981
Ile Ser Ser Asp Ile Asp Gln Leu Asn Pro Glu Ser Ala Asp Leu Arg
195                 200                 205                 210 gcc ctg gca aag cat ttg tat gac tca tac ata aag tcc ttc ccg ctg       1029
Ala Leu Ala Lys His Leu Tyr Asp Ser Tyr Ile Lys Ser Phe Pro Leu
                215                 220                 225 acc aaa gcc aag gcg agg gcg atc ttg aca gga aag aca acg gac aaa       1077
Thr Lys Ala Lys Ala Arg Ala Ile Leu Thr Gly Lys Thr Thr Asp Lys
            230                 235                 240 tca cca ttt gtc atc tac gac atg aat tcc tta atg atg gga gaa gat       1125
Ser Pro Phe Val Ile Tyr Asp Met Asn Ser Leu Met Met Gly Glu Asp
        245                 250                 255 aaa atc aag ttc aaa cat atc acc ccc ctg cag gag cag agc aaa gag       1173
Lys Ile Lys Phe Lys His Ile Thr Pro Leu Gln Glu Gln Ser Lys Glu
    260                 265                 270 gtg gcc atc cga att ttt caa ggg tgc cag ttt cga tcc gta gaa gcc       1221
Val Ala Ile Arg Ile Phe Gln Gly Cys Gln Phe Arg Ser Val Glu Ala
275                 280                 285                 290
```

-continued

| | | |
|---|---|---|
| gtg caa gag atc aca gag tat gcc aaa aat atc cct ggt ttc att aac<br>Val Gln Glu Ile Thr Glu Tyr Ala Lys Asn Ile Pro Gly Phe Ile Asn<br>                295                          300                        305 | 1269 |
| ctt gat ttg aat gac caa gtg act ctg ctc aag tat ggt gtc cat gag<br>Leu Asp Leu Asn Asp Gln Val Thr Leu Leu Lys Tyr Gly Val His Glu<br>        310                          315                        320 | 1317 |
| atc atc tac acg atg ctg gcc tcc ctg atg aat aaa gat gga gtc ctc<br>Ile Ile Tyr Thr Met Leu Ala Ser Leu Met Asn Lys Asp Gly Val Leu<br>                325                          330                        335 | 1365 |
| atc tca gag ggc caa gga ttc atg acc agg gag ttc ctc aaa agc ctg<br>Ile Ser Glu Gly Gln Gly Phe Met Thr Arg Glu Phe Leu Lys Ser Leu<br>340                          345                        350 | 1413 |
| cgg aag ccc ttt ggt gac ttt atg gag cct aag ttt gag ttt gct gtg<br>Arg Lys Pro Phe Gly Asp Phe Met Glu Pro Lys Phe Glu Phe Ala Val<br>355                          360                        365                        370 | 1461 |
| aag ttc aat gca ctg gaa tta gat gac agt gac ttg gct ata ttt ata<br>Lys Phe Asn Ala Leu Glu Leu Asp Asp Ser Asp Leu Ala Ile Phe Ile<br>                375                          380                        385 | 1509 |
| gct gtc att att ctc agt gga gac cgc cca ggc ttg ctg aac gtg aag<br>Ala Val Ile Ile Leu Ser Gly Asp Arg Pro Gly Leu Leu Asn Val Lys<br>        390                          395                        400 | 1557 |
| ccc atc gag gac atc caa gac aac ctg ctg cag gcc ctg gaa ctg cag<br>Pro Ile Glu Asp Ile Gln Asp Asn Leu Leu Gln Ala Leu Glu Leu Gln<br>                405                          410                        415 | 1605 |
| ctc aag ctg aat cac cca gag tcc tct cag ctg ttc gcc aag gtg ctc<br>Leu Lys Leu Asn His Pro Glu Ser Ser Gln Leu Phe Ala Lys Val Leu<br>420                          425                        430 | 1653 |
| cag aag atg aca gac ctc agg cag atc gtc aca gag cac gtg cag cta<br>Gln Lys Met Thr Asp Leu Arg Gln Ile Val Thr Glu His Val Gln Leu<br>435                          440                        445                        450 | 1701 |
| ctg cat gtg atc aag aag aca gag aca gac atg agc ctt cac ccc ctg<br>Leu His Val Ile Lys Lys Thr Glu Thr Asp Met Ser Leu His Pro Leu<br>                455                          460                        465 | 1749 |
| ctc cag gag atc tac aag gac ttg tat tagcaggaaa gtcccacccg<br>Leu Gln Glu Ile Tyr Lys Asp Leu Tyr<br>        470                          475 | 1796 |
| ctgacaacgt gttccttcta ttgattgcac tattattttg agggaaaaaa atctgacacc | 1856 |
| taagaaattt actgtgaaaa agcatttaaa aacaaaaagt tttagaacat gatctatttt | 1916 |
| atgcatattg tttataaaga tacatttaca atttactttt aatattaaaa attaccacat | 1976 |
| tataaaaaaa aaaaaaaaaa aggaattcc | 2005 |

<210> SEQ ID NO 2
<211> LENGTH: 475
<212> TYPE: PRT
<213> ORGANISM: Mus musculus

<400> SEQUENCE: 2

Met Val Asp Thr Glu Met Pro Phe Trp Pro Thr Asn Phe Gly Ile Ser
1               5                   10                  15

Ser Val Asp Leu Ser Val Met Glu Asp His Ser His Ser Phe Asp Ile
            20                  25                  30

Lys Pro Phe Thr Thr Val Asp Phe Ser Ser Ile Ser Ala Pro His Tyr
        35                  40                  45

Glu Asp Ile Pro Phe Thr Arg Ala Asp Pro Met Val Ala Asp Tyr Lys
    50                  55                  60

Tyr Asp Leu Lys Leu Gln Glu Tyr Gln Ser Ala Ile Lys Val Glu Pro
65                  70                  75                  80

Ala Ser Pro Pro Tyr Tyr Ser Glu Lys Thr Gln Leu Tyr Asn Arg Pro 85                  90                  95
His Glu Glu Pro Ser Asn Ser Leu Met Ala Ile Glu Cys Arg Val Cys
            100                 105                 110

Gly Asp Lys Ala Ser Gly Phe His Tyr Gly Val His Ala Cys Glu Gly
        115                 120                 125

Cys Lys Gly Phe Phe Arg Arg Thr Ile Arg Leu Lys Leu Ile Tyr Asp
130                 135                 140

Arg Cys Asp Leu Asn Cys Arg Ile His Lys Lys Ser Arg Asn Lys Cys
145                 150                 155                 160

Gln Tyr Cys Arg Phe Gln Lys Cys Leu Ala Val Gly Met Ser His Asn
                165                 170                 175

Ala Ile Arg Phe Gly Arg Met Pro Gln Ala Glu Lys Glu Lys Leu Leu
            180                 185                 190

Ala Glu Ile Ser Ser Asp Ile Asp Gln Leu Asn Pro Glu Ser Ala Asp
        195                 200                 205

Leu Arg Ala Leu Ala Lys His Leu Tyr Asp Ser Tyr Ile Lys Ser Phe
    210                 215                 220

Pro Leu Thr Lys Ala Lys Ala Arg Ala Ile Leu Thr Gly Lys Thr Thr
225                 230                 235                 240

Asp Lys Ser Pro Phe Val Ile Tyr Asp Met Asn Ser Leu Met Met Gly
                245                 250                 255

Glu Asp Lys Ile Lys Phe Lys His Ile Thr Pro Leu Gln Glu Gln Ser
            260                 265                 270

Lys Glu Val Ala Ile Arg Ile Phe Gln Gly Cys Gln Phe Arg Ser Val
        275                 280                 285

Glu Ala Val Gln Glu Ile Thr Glu Tyr Ala Lys Asn Ile Pro Gly Phe
    290                 295                 300

Ile Asn Leu Asp Leu Asn Asp Gln Val Thr Leu Leu Lys Tyr Gly Val
305                 310                 315                 320

His Glu Ile Ile Tyr Thr Met Leu Ala Ser Leu Met Asn Lys Asp Gly
                325                 330                 335

Val Leu Ile Ser Glu Gly Gln Gly Phe Met Thr Arg Glu Phe Leu Lys
            340                 345                 350

Ser Leu Arg Lys Pro Phe Gly Asp Phe Met Glu Pro Lys Phe Glu Phe
        355                 360                 365

Ala Val Lys Phe Asn Ala Leu Glu Leu Asp Asp Ser Asp Leu Ala Ile
    370                 375                 380

Phe Ile Ala Val Ile Ile Leu Ser Gly Asp Arg Pro Gly Leu Leu Asn
385                 390                 395                 400

Val Lys Pro Ile Glu Asp Ile Gln Asp Asn Leu Leu Gln Ala Leu Glu
                405                 410                 415

Leu Gln Leu Lys Leu Asn His Pro Glu Ser Ser Gln Leu Phe Ala Lys
            420                 425                 430

Val Leu Gln Lys Met Thr Asp Leu Arg Gln Ile Val Thr Glu His Val
        435                 440                 445

Gln Leu Leu His Val Ile Lys Lys Thr Glu Thr Asp Met Ser Leu His
    450                 455                 460

Pro Leu Leu Gln Glu Ile Tyr Lys Asp Leu Tyr
465                 470                 475

<210> SEQ ID NO 3
<211> LENGTH: 546
<212> TYPE: DNA
<213> ORGANISM: Saccharomyces cerevisiae
<220> FEATURE:

```
<221> NAME/KEY: CDS
<222> LOCATION: (35)...(544)

<400> SEQUENCE: 3
gggagaccca agcttgaagc aagcctcctg aaag atg aag cta ctg tct tct atc      55
                                      Met Lys Leu Leu Ser Ser Ile
                                       1               5 gaa caa gca tgc gat att tgc cga ctt aaa aag ctc aag tgc tcc aaa       103
Glu Gln Ala Cys Asp Ile Cys Arg Leu Lys Lys Leu Lys Cys Ser Lys
         10                  15                  20 gaa aaa ccg aag tgc gcc aag tgt ctg aag aac aac tgg gag tgt cgc       151
Glu Lys Pro Lys Cys Ala Lys Cys Leu Lys Asn Asn Trp Glu Cys Arg
 25                  30                  35 tac tct ccc aaa acc aaa agg tct ccg ctg act agg gca cat ctg aca       199
Tyr Ser Pro Lys Thr Lys Arg Ser Pro Leu Thr Arg Ala His Leu Thr
 40                  45                  50                  55 gaa gtg gaa tca agg cta gaa aga ctg gaa cag cta ttt cta ctg att       247
Glu Val Glu Ser Arg Leu Glu Arg Leu Glu Gln Leu Phe Leu Leu Ile
             60                  65                  70 ttt cct cga gaa gac ctt gac atg att ttg aaa atg gat tct tta cag       295
Phe Pro Arg Glu Asp Leu Asp Met Ile Leu Lys Met Asp Ser Leu Gln
     75                  80                  85 gat ata aaa gca ttg tta aca gga tta ttt gta caa gat aat gtg aat       343
Asp Ile Lys Ala Leu Leu Thr Gly Leu Phe Val Gln Asp Asn Val Asn
 90                  95                 100 aaa gat gcc gtc aca gat aga ttg gct tca gtg gag act gat atg cct       391
Lys Asp Ala Val Thr Asp Arg Leu Ala Ser Val Glu Thr Asp Met Pro
105                 110                 115 cta aca ttg aga cag cat aga ata agt gcg aca tca tca tcg gaa gag       439
Leu Thr Leu Arg Gln His Arg Ile Ser Ala Thr Ser Ser Ser Glu Glu
120                 125                 130                 135 agt agt aac aaa ggt caa aga cag ttg act gta tcg ccg gaa ttc ccg       487
Ser Ser Asn Lys Gly Gln Arg Gln Leu Thr Val Ser Pro Glu Phe Pro
                140                 145                 150 ggg atc cgt cga cgg tac cag ata tca gga tcc tgg cca gct agc tag       535
Gly Ile Arg Arg Arg Tyr Gln Ile Ser Gly Ser Trp Pro Ala Ser
            155                 160                 165 gta gct aga gg                                                         546
Val Ala Arg <210> SEQ ID NO 4
<211> LENGTH: 169
<212> TYPE: PRT
<213> ORGANISM: Saccharomyces cerevisiae

<400> SEQUENCE: 4

Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
             20                  25                  30

Lys Asn Asn Trp Glu Cys Arg Tyr Ser Pro Lys Thr Lys Arg Ser Pro
         35                  40                  45

Leu Thr Arg Ala His Leu Thr Glu Val Glu Ser Arg Leu Glu Arg Leu
     50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
            100                 105                 110
```

```
Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
        130                 135                 140

Thr Val Ser Pro Glu Phe Pro Gly Ile Arg Arg Arg Tyr Gln Ile Ser
145                 150                 155                 160

Gly Ser Trp Pro Ala Ser Val Ala Arg
                165

<210> SEQ ID NO 5
<211> LENGTH: 13
<212> TYPE: DNA
<213> ORGANISM: Mus musculus

<400> SEQUENCE: 5
aggacaaagg tca                                                          13

<210> SEQ ID NO 6
<211> LENGTH: 23
<212> TYPE: DNA
<213> ORGANISM: Mus musculus

<400> SEQUENCE: 6
ggaccaggac aaaggtcacg ttc                                               23

<210> SEQ ID NO 7
<211> LENGTH: 17
<212> TYPE: DNA
<213> ORGANISM: Saccharomyces cerevisiae

<400> SEQUENCE: 7
cggaggactg tcctccg                                                      17
```

SELECTIVE MODULATORS OF PEROXISOME PROLIFERATOR ACTIVATED RECEPTOR-GAMMA, AND METHODS FOR THE USE THEREOF

RELATED APPLICATIONS

This application is a continuation-in-part of U.S. Ser. No. 08/428,559, filed Apr. 25, 1995, now abandoned the entire contents of which are hereby incorporated by reference herein.

FIELD OF THE INVENTION

The present invention relates to methods for the modulation of nuclear receptor mediated processes. In a particular aspect, the present invention relates to the use of a specific class of compounds for the modulation of processes mediated by peroxisome proliferator activated receptor-gamma (PPAR-γ). In another aspect, the present invention relates to methods of testing compounds for their ability to regulate transcription-activating effects of PPAR-γ.

BACKGROUND OF THE INVENTION

Peroxisome proliferators are a structurally diverse group of compounds which, when administered to rodents, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, *Ann. Rev. Cell Biol.* 1:489–530 (1985); Vamecq and Draye, *Essays Biochem.* 24:1115–225 (1989); and Nelali et al., *Cancer Res.* 48:5316–5324 (1988)). Chemicals included in this group are the fibrate class of hypolipidermic drugs, herbicides, and phthalate plasticizers (Reddy and Lalwani, *Crit. Rev. Toxicol.* 12:1–58 (1983)). Peroxisome proliferation can also be elicited by dietary or physiological factors such as a high-fat diet and cold acclimatization.

Insight into the mechanism whereby peroxisome proliferators exert their pleiotropic effects was provided by the identification of a member of the nuclear hormone receptor superfamily activated by these chemicals (Isseman and Green, *Nature* 347-645–650 (1990)). This receptor, termed peroxisome proliferator activated receptor alpha (PPARα), was subsequently shown to be activated by a variety of medium and long-chain fatty acids and to stimulate expression of the genes encoding rat acyl-CoA oxidase and hydratase-dehydrogenase (enzymes required for peroxisomal β-oxidation), as well as rabbit cytochrome P450 4A6, a fatty acid ω-hydroxylase (Gottlicher et al., *Proc. Natl. Acad. Sci. USA* 89:4653–4657 (1992); Tugwood et al., *EMBO J.* 11:433–439 (1992); Bardot et al., *Biochein. Biophys. Res. Comm.* 192:37–45 (1993); Muerhoff et al., *J. Biol. Chem.* 267:19051–19053 (1992); and Marcus et al., *Proc. Natl. Acad. Sci. USA* 90(12): 5723–5727 (1993).

The above-noted references suggest a physiological role for PPARα in the regulation of lipid metabolism. PPARα activates transcription by binding to DNA sequence elements, termed peroxisome proliferator response elements (PPRE), as a heterodimer with the retinoid X receptor. The retinoid X receptor is activated by 9-cis retinoic acid (see Kliewer et al., *Nature* 358:771–774 (1992), Gearing et al., *Proc. Natl. Acad. Sci. USA* 90:1440–1444 (1993), Keller et al., *Proc. Natl. Acad. Sci. USA* 90:2160–2164 (1993), Heyman et al., *Cell* 68:397–406 (1992), and Levin et al., *Nature* 355:359–361 (1992)). Since the PPARα-RXR complex can be activated by peroxisome proliferators and/or 9-cis retinoic acid, the retinoid and fatty acid signaling pathways are seen to converge in modulating lipid metabolism.

Since the discovery of PPARα, additional isoforms of PPAR have been identified, e.g., PPARβ, PPARγ and PPARδ, which are spatially differentially expressed. Because there are several isoforms of PPAR, it would be desirable to identify compounds which are capable of selectively interacting with only one of the PPAR isoforms. Such compounds would find a wide variety of uses, such as, for example, in the prevention of obesity, for the treatment of diabetes, and the like.

BRIEF DESCRIPTION OF THE INVENTION

In accordance with the present invention, we have identified a class of compounds which are capable of selectively modulating processes mediated by peroxisome proliferator activated receptor-gamma (PPAR-γ). The identification of such compounds makes possible the selective intervention in PPARγ mediated pathways, without exerting inadvertent effects on pathways mediated by other PPAR isoforms.

DETAILED DESCRIPTION OF THE INVENTION

Figure 1:
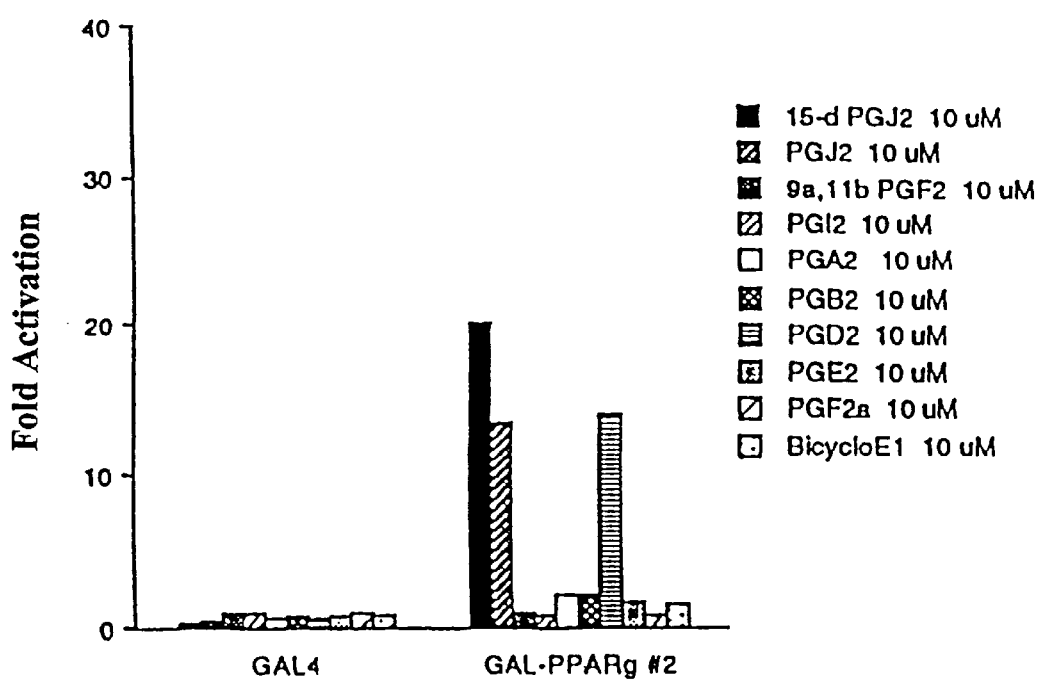
FIG. 1 illustrates the activation of a GAL4-PPARγ fusion protein by a variety of prostaglandin or prostaglandin-like compounds. In the figure, black bars represent 15-deoxy-$\Delta^{12,14}$-prostaglandin-J$_2$ (15-d PGJ2), the dark, striped bars represent prostaglandin-J$_2$ (PGJ2), the darkly shaded bars represent 9α,11β-prostaglandin-F$_2$ (9a,11bPGF2), the light, closely (diagonally) striped bars represent prostaglandin-I$_2$ (PGI2), the open bars represent prostaglandin-A$_2$ (PGA2), the dark bars with light dots represent prostaglandin-B$_2$ (PGB2), the horizontally hatched bars represent prostaglandin-D$_2$ (PGD2), the light bars with dark dots represent prostaglandin-E$_2$ (PGE2), the light, sparsely (diagonally) hatched bars represent prostaglandin-F$_{2\alpha}$ (PGF2a), and the light bars with sparsely spaced dots represent bicycloprostaglandin-E$_1$ (BicycloE1).

In accordance with the present invention, there are provided methods for modulating process(es) mediated by peroxisome proliferator activated receptor-gamma (PPAR-γ), said method comprising conducting said process(es) in the presence of at least one PPAR-γ-selective prostaglandin or prostaglandin-like compound or precursor thereof.

PPAR-γ-selective prostaglandins or prostaglandin-like compounds contemplated for use in the practice of the present invention include members of the prostaglandin-J$_2$ family of compounds (e.g., prostaglandin-J$_2$, $\Delta^{12}$-prostaglandin-J$_2$ or 15-deoxy-$\Delta^{12,14}$-prostaglandin-J$_2$) members of the prostaglandin-D$_2$ family of compounds (e.g., prostaglandin-D$_2$), or precursors thereof, as well as compounds having the structure I:

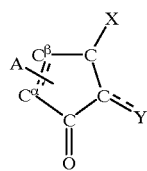

(I)

wherein:
A is selected from hydrogen or a leaving group at the α- or β-position of the ring, or A is absent when there is a double bond between C<sup>α</sup> and C<sup>β</sup> of the ring;

X is an alkyl, substituted alkyl, alkenyl, substituted alkenyl, alkynyl or substituted alkynyl group having in the range of 2 up to 15 carbon atoms; and Y is an alkyl, substituted alkyl, alkenyl, substituted alkenyl, alkynyl or substituted alkynyl group having in the range of 2 up to 15 carbon atoms.

As employed herein, the term "leaving group" refers to functional groups which can readily be removed from the precursor compound, for example, by nucleophilic displacement, under $E_2$ elimination conditions, and the like. Examples include hydroxy groups, alkoxy groups, tosylates, brosylates, halogens, and the like.

As employed herein, "lower alkyl" refers to straight or branched chain alkyl groups having in the range of about 1 up to 4 carbon atoms; "alkyl" refers to straight or branched chain alkyl groups having in the range of about 1 up to 12 carbon atoms; "substituted alkyl" refers to alkyl groups further bearing one or more substituents such as hydroxy, alkoxy (of a lower alkyl group), mercapto (of a lower alkyl group), halogen, trifluoromethyl, cyano, nitro, amino, carboxyl, carbamate, sulfonyl, sulfonamide, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "alkenyl" refers to straight or branched chain hydrocarbyl groups having at least one carbon-carbon double bond, and having in the range of about 2 up to 12 carbon atoms and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "acyl" refers to alkyl-carbonyl species.

As employed herein, "halogen" or "halo" refers to fluoro substituents, chloro substituents, bromo substituents or iodo substituents.

In a presently preferred aspect of the present invention, "X" of Formula I is selected from:
—(CRR)$_m$—Z,
—(CRR)$_{m'}$—C(R)=C(R)—(CRR)$_{m'}$—Z, or
—(CRR)$_{m''}$—C≡C—(CRR)$_{m''}$—Z, wherein:
each R is independently selected from H, lower alkyl, substituted lower alkyl, hydroxy, lower alkoxy, thioalkyl, halogen, trifluoromethyl, cyano, nitro, amino, carboxyl, carbamate, sulfonyl or sulfonamide,
m falls in the range of 1 up to 15,
each m' falls independently in the range of 0 up to 12, with the proviso that the total chain length of the alkenyl moiety does not exceed 15 carbon atoms,
each m" falls independently in the range of 0 up to 12, with the proviso that the total chain length of the alkynyl moiety does not exceed 15 carbon atoms, and
Z is a polar, heteroatom-containing substituent.

Those of skill in the art can readily identify numerous groups which satisfy the requirement that Z be a polar, heteroatom-containing (i.e., O, N, S, or the like) substituent. Thus, Z can be selected from cyano, nitro, amino, carbamate, or a substituent having the structure:
—CH$_2$OR', wherein R' is selected from H, alkyl, alkenyl, alkynyl, acyl, aryl, or the like;
—C(O)R", wherein R" is selected from H, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl,
—CO$_2$R'", wherein R'" is selected from H, alkyl, alkenyl, alkynyl, or the like;
—SR', —S(O)R', —S(O)$_2$R' or —S(O)$_2$NHR', wherein each R' is as defined above,
and the like.

Especially preferred compounds employed in the practice of the present invention are those wherein "X" of Formula I is
—CRR—C(R)=C(R)—(CRR)$_m$—Z, wherein:
each R is independently selected from H, lower alkyl, substituted lower alkyl, hydroxy, alkoxy (of a lower alkyl group), halogen, trifluoromethyl, amino, carboxyl or sulfonyl,
m falls in the range of 1 up to 6, and
Z is selected from —CH$_2$OH, —CH$_2$OAc, —CO$_2$H, —CO$_2$Me or —CO$_2$Et.

In another preferred aspect of the present invention, "Y" of Formula I is selected from:

=C(R)—[C(R)=C(R)]$_n$—(CRR)$_{n'}$—Z' (II),

=C(R)—[C≡C]$_{n''}$—(CRR)$_{n'}$—Z' (IIA),

=C(R)—CRR—CR(R')—(CRR)$_{n'}$—Z' (III),

—[C(R)=C(R)]$_n$—(CRR)$_{n'}$—Z' (IV), or

—[C≡C]$_{n''}$—(CRR)$_{n'}$—Z' (IVA), wherein
  each R is independently as defined above,
  each R' is independently selected from H, lower alkyl, substituted lower alkyl or a leaving group,
  Z' is selected from H, lower alkyl or substituted lower alkyl,
  n falls in the range of 0 up to 4,
  n' falls in the range of 2 up to 12, and
  n'' falls in the range of 1 up to 3.

Especially preferred compounds contemplated for use in the practice of the present invention include those wherein "Y" of Formula I is selected from:

=C(R)—C(R)=C(R)—(CRR)$_{n'}$—Z' (II),

=C(R)—CRR—CR(R')—(CRR)$_{n'}$—Z' (III), or

—C(R)=C(R)—CR(R')—(CRR)$_{n'}$—Z' (IV), wherein
  each R is independently as defined above,
  each R' is independently as defined above,
  Z' is selected from H, lower alkyl or substituted lower alkyl, and
  n' falls in the range of 1 up to 6.

Presently most preferred compounds for use in the practice of the present invention include those wherein "Y" of Formula I is =C(R)—C(R)=C(R)—(CRR)$_n$Z' (II), wherein each R is selected from H, lower alkyl or substituted lower alkyl, n is 1, n' falls in the range of about 2 up to 6, and Z' is selected from H or lower alkyl; or those wherein "Y" of Formula I is =C(R)—CRR—CR(R')—(CRR)$_{n'}$—Z' (III) or —C(R)=C(R)—CR(R')—(CRR)$_{n'}$—Z' (IV), wherein each R is selected from H, lower alkyl or substituted lower alkyl, R' is selected from H, lower alkyl, or an hydroxy group, n is 1, n' falls in the range of about 2 up to 6, and Z' is selected from H or lower alkyl.

Referring to the structural formulae set forth above, prostaglandin-D$_2$ (Pg-D2) is described by Formula I (as set forth above), wherein A is 9—OH, Y is IV, each R is hydrogen, R' is hydroxy, Z is —CO$_2$H, m is 3, Z' is methyl, n is 1 and n' is 4; prostaglandin-J$_2$ (Pg-J2) is described by Formula I, wherein A is absent, Y is IV, each R is hydrogen, R' is hydroxy, Z is —CO$_2$H, m is 3, Z' is methyl, n is 1 and n' is 4; $\Delta^{12}$-prostaglandin-J$_2$ ($\Delta^{12}$-Pg-J2) is described by Formula I, wherein A is absent, Y is III, each R is hydrogen, R' is hydroxy, Z is —CO$_2$H, m is 3, Z' is methyl, n is 1 and n' is 4; 15-deoxy-$\Delta^{12,14}$-prostaglandin-J$_2$ (15-deoxy-$\Delta^{12,14}$-Pg-J2) is described by Formula I, wherein A is absent, Y is II, each R is hydrogen, Z is —CO$_2$H, m is 3, Z' is methyl, n is 1 and n' is 4.

The above-described compounds can be readily prepared using a variety of synthetic methods, as are well known by those of skill in the art. For example, many of the above-described compounds can be prepared chemically or enzymatically, from the naturally occurring precursor, arachidonic acid.

As employed herein, the term "modulate" refers to the ability of a modulator for a member of the steroid/thyroid superfamily to either directly (by binding to the receptor as a ligand) or indirectly (as a precursor for a ligand or an inducer which promotes production of ligand from a precursor) induce expression of gene(s) maintained under hormone expression control, or to repress expression of gene(s) maintained under such control.

As employed herein, the phrase "processes mediated by PPARγ" refers to biological, physiological, endocrinological, and other bodily processes which are mediated by receptor or receptor combinations which are responsive to the PPAR-γ-selective prostaglandin or prostaglandin-like compounds described herein. Modulation of such processes can be accomplished in vitro or in vivo. In vivo modulation can be carried out in a wide range of subjects, such as, for example, humans, rodents, sheep, pigs, cows, and the like.

PPAR-γ-selective prostaglandin or prostaglandin-like compounds contemplated for use in the practice of the present invention can be employed for both in vitro and in vivo applications. For in vivo applications, the invention compounds can be incorporated into a pharmaceutically acceptable formulation for administration. Those of skill in the art can readily determine suitable dosage levels when compounds contemplated for use in the practice of the present invention are so used.

In accordance with another embodiment of the present invention, there is provided a method of testing compound (s) for the ability to regulate the transcription-activating effects of a peroxisome proliferator activated receptor-gamma (PPAR-γ), said method comprising assaying for changes in the level of reporter protein present as a result of contacting cells containing said receptor and reporter vector with said compound;
  wherein said reporter vector comprises:
    (a) a promoter that is operable in said cell,
    (b) a hormone response element, and
    (c) a DNA segment encoding a reporter protein,
      wherein said reporter protein-encoding DNA segment is operatively linked to said promoter for transcription of said DNA segment, and
      wherein said hormone response element is operatively linked to said promoter for activation thereof.

Hormone response elements contemplated for use in the practice of the present invention are composed of at least one direct repeat of two or more half sites separated by a spacer of one nucleotide. The spacer nucleotide can be selected from any one of A, C, G or T. Each half site of response elements contemplated for use in the practice of the invention comprises the sequence

—RGBNNM—, wherein
  R is selected from A or G;
  B is selected from G, C, or T;
  each N is independently selected from A, T, C, or G; and
  M is selected from A or C;
  with the proviso that at least 4 nucleotides of said —RGBNNM—sequence are identical with the nucleotides at corresponding positions of the sequence —AGGTCA—. Response elements employed in the practice of the present invention can optionally be preceded by N$_x$, wherein x falls in the range of 0 up to 5.

Presently preferred response elements contain at least one copy (with one, two or three copies most common) of the minimal sequence:

AGGACA A AGGTCA (SEQ ID NO:4).

As noted above, the minimal sequence can optionally be flanked by additional residues, for example, as in the sequence:

GGACC AGGACA A AGGTCA CGTTC (SEQ ID NO:5).

In a preferred embodiment of the present invention, only the ligand binding domain of PPARγ is utilized, in combination with the DNA binding domain of GAL4 protein, for the identification of PPARγ ligands or ligand-precursors. This allows one to avoid possible background signal caused by the potential presence of endogenous PPARγ in the host cells used for the assay.

The DNA binding domain of the yeast GAL4 protein comprises at least the first 74 amino acids thereof (see, for example, Keegan et al., Science 231:699–704 (1986)). Preferably, the first 90 or more amino acids of the GAL4 protein will be used, with the first 147 amino acid residues of yeast GAL4 being presently most preferred.

The GAL4 fragment employed in the practice of the present invention can be incorporated into any of a number of sites within the PPARγ receptor protein. For example, the GAL4 DNA binding domain can be introduced at the amino terminus of the PPARγ receptor protein, or the GAL4 DNA binding domain can be substituted for the native DNA binding domain of the PPARγ receptor, or the GAL4 DNA binding domain can be introduced at the carboxy terminus of the PPARγ receptor protein, or at other positions as can readily be determined by those of skill in the art. Thus, for example, a modified receptor protein can be prepared which consists essentially of amino acid residues 1–147 of GAL4, plus the ligand binding domain of PPARγ (i.e., containing the ligand binding domain only of said receptor (i.e., residues 163–475 of SEQ ID NO:1), substantially absent the DNA binding domain and amino terminal domain thereof).

Identification methods according to the present invention involve the use of a functional bioassay system, wherein the modified receptor and a reporter plasmid are cultured in suitable host cells in the presence of test compound. Evidence of transcription (e.g., expression) of reporter gene is then monitored to determine the presence of an activated receptor-ligand complex. Accordingly, the functional bioassay system utilizes two plasmids: an "expression" plasmid and a "reporter" plasmid. The expression plasmid can be any plasmid which contains and is capable of expressing DNA encoding the desired form of PPARγ receptor protein (i.e., intact receptor or GAL4 chimeric receptor as described hereinabove), in a suitable host cell. The reporter plasmid can be any plasmid which contains an operative PPRE or GAL4 response element, as appropriate, functionally linked to an operative reporter gene.

Exemplary PPREs have been described in detail hereinabove. Exemplary GAL4 response elements are those containing the palindromic 17-mer:

5'-CGGAGGACTGTCCTCCG-3' (SEQ ID NO:6), such as, for example, 17MX, as described by Webster et al., in Cell 52:169–178 (1988), as well as derivatives thereof. Additional examples of suitable response elements include those described by Hollenberg and Evans in Cell 55:899–906 (1988); or Webster et al. in Cell 54:199–207 (1988).

Exemplary reporter genes include chloramphenicol transferase (CAT), luciferase (LUC), beta-galactosidase (β-gal), and the like. Exemplary promoters include the simian virus (SV) promoter or modified form thereof (e.g., ΔSV), the thymidine kinase (TK) promoter, the mammary tumor virus (MTV) promoter or modified form thereof (e.g., ΔMTV), and the like [see, for example, Mangelsdorf et al., in Nature 345:224–229 (1990), Mangelsdorf et al., in Cell 66:555–561 (1991), and Berger et al., in J. Steroid Biochem. Molec. Biol. 41:733–738 (1992)]. The plasmids pGMCAT, pGHCAT, pTK-GAL$_p$3-LUC, ΔMTV-GAL$_p$3-LUC, ΔMTV-GAL$_p$3-CAT, and the like, are examples of reporter plasmids which contain an operative hormone responsive promoter/enhancer element functionally linked to an operative reporter gene, and can therefore be used in the above-described functional bioassay (see Example 2 for details on the preparation of these plasmids). In pGMCAT, the operative hormone responsive promoter/enhancer element is the MTV LTR; in pGHCAT it is the functional portion of the growth hormone promoter. In both PGMCAT and GHCAT the operative reporter gene is the bacterial gene for chloramphenicol acetyltransferase (CAT).

As used herein in the phrase "operative response element functionally linked to an operative reporter gene", the word "operative" means that the respective DNA sequences (represented by the terms "PPRE," "GAL4 response element" and "reporter gene") are operational, i.e., work for their intended purposes; the word "functionally" means that after the two segments are linked, upon appropriate activation by a ligand-receptor complex, the reporter gene will be expressed as the result of the fact that the "PPRE" or "GAL4 response element" was "turned on" or otherwise activated.

In practicing the above-described functional bioassay, the expression plasmid and the reporter plasmid are co-transfected into suitable host cells. The transfected host cells are then cultured in the presence and absence of a test compound to determine if the test compound is able to produce activation of the promoter operatively linked to the PPRE or GAL4 response element of the reporter plasmid. Thereafter, the transfected and cultured host cells are monitored for induction (i.e., the presence) of the product of the reporter gene sequence.

Any cell line can be used as a suitable "host" for the functional bioassay contemplated for use in the practice of the present invention. Thus, in contrast to the requirements of prior art assay systems, when GAL4 chimerics are employed, there is no need to use receptor-negative cells in carrying out the invention process. Since the modified receptor employed in the practice of the present invention is the only species in the test cell which is capable of initiating transcription from a GAL4 response element, the expression of native receptor by the test cell does not contribute to background levels. Thus, the invention bioassay can be made to be very selective.

Cells contemplated for use in the practice of the present invention include transformed cells, non-transformed cells, neoplastic cells, primary cultures of different cell types, and the like. Exemplary cells which can be employed in the practice of the present invention include Schneider cells, CV-1 cells, HuTu80 cells, F9 cells, NTERA2 cells, NB4 cells, HL-60 cells, 293 cells, Hela cells, yeast cells, and the like. Preferred host cells for use in the functional bioassay system are COS cells and CV-1 cells. COS-1 (referred to as COS) cells are monkey kidney cells that express SV40 T antigen (Tag); while CV-1 cells do not express SV40 Tag. The presence of Tag in the COS-1 derivative lines allows the introduced expression plasmid to replicate and provides a relative increase in the amount of receptor produced during the assay period. CV-1 cells are presently preferred because they are particularly convenient for gene transfer studies and provide a sensitive and well-described host cell system.

The above-described cells (or fractions thereof) are maintained under physiological conditions when contacted with physiologically active compound. "physiological conditions" are readily understood by those of skill in the art to comprise an isotonic, aqueous nutrient medium at a temperature of about 370° C.

In accordance with another embodiment of the present invention, there is provided a method of screening for antagonists of PPARγ receptor proteins, said method comprising culturing test cells containing
(i) increasing concentrations of at least one compound whose ability to inhibit the transcription activation activity of PPARγ agonists is sought to be determined, and
(ii) optionally, at least one PPARγ agonist,
wherein said test cells contain
(i) exogenous DNA which expresses intact PPARγ or a modified form of PPARγ, wherein the modified form of PPARγ contains the DNA binding domain of GAL4, and
(ii) a PPRE or GAL4 response element, respectively, operatively linked to a reporter gene; and thereafter assaying for evidence of transcription of said reporter gene in said cells as a function of the concentration of said compound in said culture medium, thereby indicating the ability of said compound to inhibit activation of transcription by PPARγ agonists.

Media employed for such culturing may include agonist for the receptor being tested, or the receptor may be constitutive (i.e., not require the presence of agonist for activation), or a fixed concentration of agonist can be added to the media employed for such testing.

The above-described assays of the present invention have low background and a broad dynamic range.

In accordance with yet another embodiment of the present invention, there is provided a method for preventing obesity, said method comprising administering to a subject in need thereof an amount of a peroxisome proliferator activated receptor-gamma (PPAR-γ) antagonist effective to block cell differentiation to produce lipid-accumulating cells.

As employed here, "obesity" refers generally to individuals who are at least about 20–30% over the average weight for his/her age, sex and height. Technically, "obese" is defined, for males, as individuals whose body mass index is greater than 27.8 kg/m², and for females, as individuals whose body mass index is greater than 27.3 kg/m².

Those of skill in the art recognize that there are numerous cell types which are capable of differentiation to produce "lipid-accumulating cells," such as, for example, mesenchymal cells (e.g., fibroblasts).

As employed herein, the phrase "amount . . . effective to block cell differentiation" refers to levels of compound sufficient to provide circulating concentrations high enough to effect activation of PPARγ. Such a concentration typically falls in the range of about 10 nM up to 2 μM; with concentrations in the range of about 100 nM up to 200 nM being preferred.

In accordance with a particular embodiment of the present invention, compositions comprising at least one prostaglandin or prostaglandin-like compound (as described above), and a pharmaceutically acceptable carrier are contemplated. Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

In accordance with still another embodiment of the present invention, there is provided a method for treating diabetes, said method comprising administering to a subject in need thereof an amount of a peroxisome proliferator activated receptor-gamma (PPAR-γ) agonist effective to lower the blood glucose level of said subject.

As employed herein, the phrase "amount . . . effective to lower blood glucose levels" refers to levels of compound sufficient to provide circulating concentrations high enough to accomplish the desired effect. Such a concentration typically falls in the range of about 10 nM up to 2 μM; with concentrations in the range of about 100 nM up to 200 nM being preferred.

The invention will now be described in greater detail by reference to the following non-limiting examples.

Example 1

Preparation of GAL4-receptor fusion proteins

A basic vector useful for the generation of GAL4-receptor fusion proteins is called pCMX-GAL4 (see SEQ ID NO:2). This vector encodes GAL4 DNA binding domain, followed by a polylinker sequence useful in the cloning. The parental expression vector pCMX has been described by Umesono et al., in Cell 65:1255–1266 (1991), and the GAL4 portion of pCMX-GAL4 is derived from plasmid pSG424, described by Sadowski and Ptashne, in Nucleic Acids Res. 17:7539 (1989).

In general, GAL4-receptor ligand binding domain fusions are prepared by taking advantage of mutant receptor cDNA clones, such as GR-RAR chimera [see, for example, Giguere et al., in Nature 330:624–629 (1987)]. These mutant receptor cDNAs encode common XhoI sites at the end of the DNA binding domain, as described by Giguere et al., supra. To do so, a new pCMX-GAL4 vector was prepared which encodes a compatible SalI site in the polylinker sequence (there is an XhoI site in the GAL4 sequence):

SalI site: G'TCGAC

XhoI site: C'TCGAG

This allows efficient transfer of the receptor ligand binding domain to GAL4 DNA binding domain. Through this method, a number of chimeric species have been generated, including GAL4-PPARγ, containing residues 163–475 of PPARγ (see SEQ ID NO:1).

If mutants of the type referred to above are not available for the construction of GAL4-containing chimerics, one may simply look for any convenient restriction enzyme site within or downstream of the DNA binding domain of the receptor of interest (i.e., within about the first 30 amino acid residues downstream of the conserved Gly-Met residues of the DNA binding domain, i.e., within 30 residues of the last two residues shown in SEQ ID NO:1), and utilize the carboxy terminal sequences therefrom.

Example 2

Preparation of Reporter Constructs

Various reporter constructs are used in the examples which follow. They are prepared as follows:

TK-LUC: The MTV-LTR promoter sequence was removed from the MTV-LUC plasmid described by Hollenberg and Evans in Cell 55:899–906 (1988) by HindIII and XhoI digest, and cloned with the HindIII-XhoI fragment of the Herpes simplex virus thymidine kinase gene promoter (−105 to +51 with respect to the transcription start site, m, isolated from plasmid pBLCAT2, described by Luckow & Schutz in Nucleic Acids Res. 15:5490 (1987)) to generate parental construct TK-LUC.

pTK-PPRE3-LUC: Three copies of double-stranded peroxisome proliferator response element (PPRE) oligonucleotides (see SEQ ID NO:3) were cloned upstream of the TK promoter of TK-LUC at the SalI site.

pTK-MH100x4-LUC: Four copies of double-stranded MH100 oligonucleotides, encoding a GAL4 binding site, were cloned upstream of the TK promoter of TK-LUC at the HindIII site.

CMX-βGAL: The coding sequence for the *E. coli* β-galactosidase gene was isolated from plasmid pCH110 [see Hall et al., J. Mol. Appl. Genet. 2:101–109 (1983)] by HindIII and BamHI digest, and cloned into pCMX eucaryotic expression vector [see Umesono et al., supra].

Example 3

Screening Assay for Receptor Selective Agonists

CV-1 cells are co-transfected with CMX-GAL-PPARγ and pTK-MH100x4-LUC at a ratio of about 100 ng of receptor-encoding DNA per $10^5$ cells. The usual amounts of DNA per $10^5$ cells are 100 ng of CMX-GAL-PPARγ, 300 ng of pTK-MH100x4-LUC, and 500 ng of CMX-βGAL. Typically, transfections are performed in triplicate. The plates are then incubated for 2–3 hours at 370° C.

The cells are washed with fresh medium. Fresh medium containing one concentration of a serial dilution of agonist is added to each well. A typical agonist dilution series extends from $10^{-5}$M through $10^{-11}$M. A solvent control is performed for each agonist. The cells are incubated at 37° C. for 1–2 days.

The cells are rinsed twice with buffered saline solution. Subsequently, cells are lysed, in situ, by adding 200 μl of lysis buffer. After 30 minutes incubation at room temperature, 40 μl aliquots of cell lysate are transferred to 96-well plates for luciferase reporter gene assays and μ-galactosidase transfection controls [see Heyman et al., Cell 68:397–406 (1992)].

The data are expressed as relative light units (RLUs) per O.D. unit of μ-galactosidase per minute. The triplicates are averaged for each concentration and plotted (see FIG. 1) as fold induction induced by a standard dose (10 μM) of agonist.

Example 4

Dose Response of GAL4-PPARγ Constructs to Various Prostaglandins

Effector plasmid, reporter plasmid, and μ-galactosidase control plasmid are co-transfected into CV-1 cells at a ratio of about 1:3:5, using a liposome-mediated method, employing N-{2-(2,3)-dioleoyloxy)propyl-N,N,N-trimethyl ammonium methyl sulfate} (i.e., DOTAP, Boehringer Mannheim) according to the manufacturer's instructions in Dulbecco's modified Eagle's medium (DMEM) with 10% delipidated hormone-depleted fetal calf serum. After about 2–3 hours, the cells are washed with DMEM and an appropriate prostaglandin is added to the media to the final molar concentration indicated in FIG. 2. After 24–48 hours of incubation, the cells are rinsed with phosphate buffered saline (pH 7.2) and lysed. Aliquots are assayed for luciferase and μ-galactosidase activity. Luciferase activity is normalized to optical density units of μ-galactosidase per minute of incubation.

Figure 2:
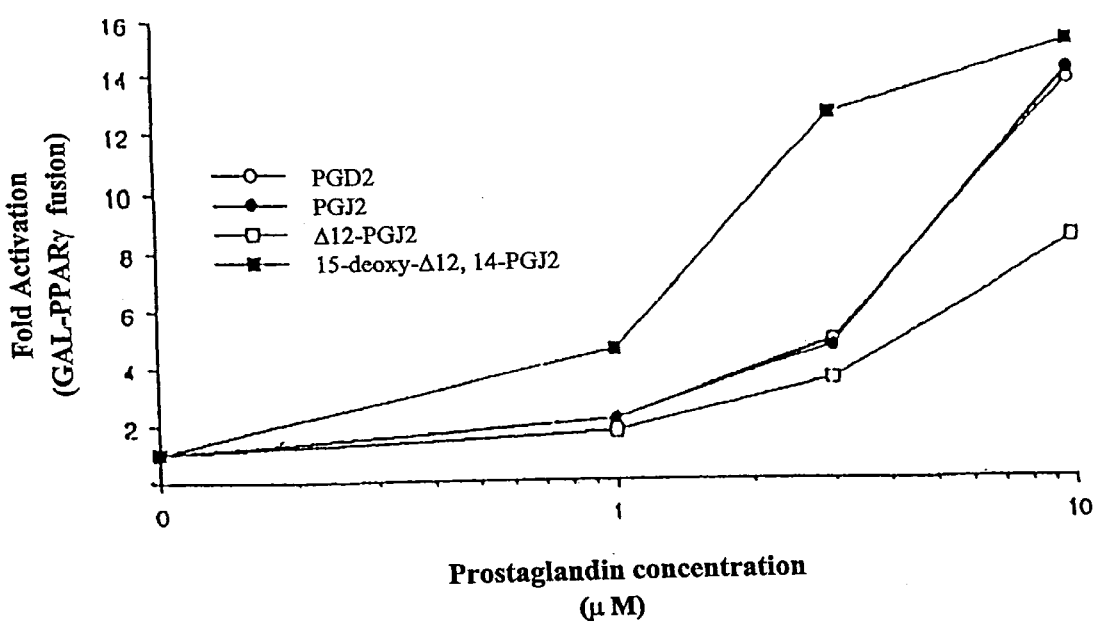
FIG. 2 illustrates the dose response for activation of a GAL4-PPARγ fusion protein by a variety of prostaglandin or prostaglandin-like compounds. In the figure, open circles represent prostaglandin-D$_2$ (PGD2), darkened circles represent prostaglandin-J$_2$ (PGJ2), open squares represent $\Delta^{12}$-prostaglandin-J$_2$ ($\Delta$12-PGJ2), and darkened squares represent 15-deoxy-$\Delta^{12,14}$-prostaglandin-J$_2$ (15-deoxy-$\Delta$12,14-PGJ2).

The data are expressed in FIG. 2 as fold induction over the same construct incubated in solvent alone. Review of FIG. 2 reveals that PGD2 and PGJ2 families of compounds are functional modulators of PPARγ.

While the invention has been described in detail with reference to certain preferred embodiments thereof, it will be understood that modifications and variations are within the spirit and scope of that which is described and claimed.

That which is claimed is:

1. A method for modulating process(es) mediated by peroxisome proliferator activated receptor-gamma (PPAR-γ), said method comprising conducting said process(es) in the presence of an amount of at least one PPAR-γ-selective prostaglandin or prostaglandin-like compound or precursor thereof sufficient to modulate said process(es), wherein said PPAR-γ-selective prostaglandin or prostaglandin-like compound or precursor thereof is a prostaglandin-$J_2$, a prostaglandin-$D_2$, a precursor of prostaglandin-$J_2$ or prostaglandin-$D_2$, or structure I, wherein structure I is defined as follows:

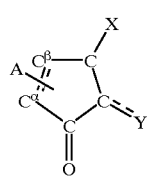

(I)

wherein:
A is hydrogen or a leaving group at the α- or β-position of the ring, or A is absent when there is a double bond between $C^α$ and $C^β$ of the ring;

X is an alkyl, substituted alkyl, alkenyl, substituted alkenyl, alkynyl or substituted alkynyl group having in the range of 2 up to 15 carbon atoms; and Y is an alkyl, substituted alkyl, alkenyl, substituted alkenyl, alkynyl or substituted alkynyl group having in the range of 2 up to 15 carbon atoms;

provided, however, that A is not hydroxy when:

X is:
—$(CH_2)_6$—COOH, and
Y is
—CH=CH—CH(OH)—$(CH_2)_4$—$CH_3$, or
—$(CH_2)_2$—CH(OH)—$(CH_2)_4$—$CH_3$, or X is
—$CH_2$—CH=CH—$(CH_2)_3$—COOH, and
Y is
—CH=CH—CH(OH)—$(CH_2)_4$—$CH_3$, or
—CH=CH—CH(OH)—$CH_2$—CH=CH—$CH_2$—$CH_3$.

2. A method according to claim 1 wherein said PPAR-γ-selective prostaglandin is selected from a prostaglandin-$J_2$, a prostaglandin-$D_2$, or a precursor thereof.

3. A method according to claim 2 wherein said prostaglandin-$J_2$ is selected from prostaglandin-$J_2$, $Δ^{12}$-prostaglandin-$J_2$ or 15-deoxy-$Δ^{12,14}$-prostaglandin-$J_2$.

4. A method according to claim 1, wherein said PPAR-γ-selective prostaglandin or prostaglandin-like compound has the structure I.

5. A method according to claim 4 wherein:
X of Formula I is selected from:
—$(CRR)_m$—Z,
—$(CRR)_{m'}$—C(R)=C(R)—$(CRR)_{m'}$—Z, or
—$(CRR)_{m''}$—C≡C—$(CRR)_{m''}$—Z, wherein:

each R is independently selected from hydrogen, lower alkyl, substituted lower alkyl, hydroxy, lower alkoxy, thioalkyl, halogen, trifluoromethyl, cyano, nitro, amino, carboxyl, carbamate, sulfonyl or sulfonamide, m falls in the range of 1 up to 15, each m' falls independently in the range of 0 up to 12, with the proviso that the total chain length of the alkenyl moiety does not exceed 15 carbon atoms, each m" falls independently in the range of 0 up to 12, with the proviso that the total chain length of the alkynyl moiety does not exceed 15 carbon atoms, and Z is a polar, heteroatom-containing substituent; and Y of Formula I is selected from:
=C(R)—[C(R)=C(R)]$_n$—(CRR)$_{n'}$—Z' (II),
=C(R)—[C≡C]$_{n''}$—(CRR)$_{n'}$—Z' (IIA),
=C(R)—CRR—CR(R')—(CRR)$_{n'}$—Z' (III),
—[C(R)≡C(R)]$_n$—(CRR)$_{n'}$—Z' (IV),
—[C≡C]$_n$—(CRR)$_{n'}$—Z' (IVA),
wherein
each R is independently as defined above,
each R' is independently selected from H, lower alkyl, substituted lower alkyl, or a leaving group,
Z' is selected from H, lower alkyl or substituted lower alkyl,
n falls in the range of 0 up to 4,
n' falls in the range of 2 up to 12, and
n" falls in the range of 1 up to 3.

6. A method according to claim 5 wherein Z is selected from cyano, nitro, amino, carbamate, or a substituent having the structure:

—CH$_2$OR', wherein R' is selected from H, alkyl, alkenyl, alkynyl, acyl or aryl;

—C(O)R", wherein R" is selected from H, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl, —CO$_2$R'", wherein R'" is selected from H, alkyl, alkenyl or alkynyl;

—SR', —S(O)R', —S(O)$_2$R' or —S(O)$_2$NHR', wherein each R' is as defined above.

7. A method according to claim 5 wherein:

X of Formula I is —CRR—C(R)=C(R)—(CRR)$_m$—Z, wherein:
each R is independently selected from hydrogen, lower alkyl, substituted lower alkyl, hydroxy, alkoxy (of a lower alkyl group), halogen, trifluoromethyl, amino, carboxyl, or sulfonyl, m falls in the range of 1 up to 6, and Z is selected from —CH$_2$OH, —CH$_2$OAc, —CO$_2$H, —CO$_2$Me or —CO$_2$Et; and Y of Formula I is selected from:
=C(R)—C(R)=C(R)—(CRR)$_{n'}$—Z' (II),
=C(R)—CRR—CR(R')—(CRR)$_{n'}$—Z' (III), or
—C(R)=C(R)—CR(R')—(CRR)$_{n'}$—Z' (IV), wherein
each R is independently as defined above,
each R' is independently selected from H, lower alkyl, substituted lower alkyl, or a leaving group,
Z' is selected from H, lower alkyl or substituted lower alkyl, and
n' falls in the range of 1 up to 6.

8. A method according to claim 7 wherein Y of Formula I is
=C(R)—C(R)=C(R)—(CRR)$_{n'}$—Z' (II),
wherein each R is selected from hydrogen, lower alkyl or substituted lower alkyl, n is 1, n' falls in the range of about 2 up to 6, and Z' is selected from hydrogen or lower alkyl.

9. A method according to claim 7 wherein Y of Formula I is
=C(R)—CRR—CR(R')—(CRR)$_{n'}$—Z' (III) or
—C(R)=C(R)—CR(R')—(CRR)$_{n'}$—Z' (IV),
wherein each R is selected from hydrogen, lower alkyl or substituted lower alkyl, R' is selected from hydrogen, lower alkyl, or an hydroxy group, n is 1, n' falls in the range of about 2 up to 6, and Z' is selected from hydrogen or lower alkyl.

10. A method according to claim 5 wherein A is 9—OH, Y is IV, each R is hydrogen, R' is hydroxy, Z is —CO$_2$H, m=3, Z' is methyl, n=1 and n'=4.

11. A method according to claim 5 wherein A is absent, Y is IV, each R is hydrogen, R' is hydroxy, Z is —CO$_2$H, m is 3, Z' is methyl, n=1 and n'=4.

12. A method according to claim 5 wherein A is absent, Y is II, each R is hydrogen, R' is hydroxy, Z is —CO$_2$H, m=3, Z' is methyl, n=1 and n'=4.

13. A method according to claim 5 wherein A is absent, Y is I, each R is hydrogen, Z is —CO$_2$H, m=3, Z' is methyl, n=1 and n'=4.

14. A method according to claim 1 wherein said process mediated by PPAR-γ is cell differentiation to produce lipid-accumulating cells.

15. A method according to claim 1 wherein said process mediated by PPAR-γ is the response of the recipient to insulin.

* * * * *